(12) United States Patent
Inoue et al.

(10) Patent No.: US 10,206,979 B2
(45) Date of Patent: Feb. 19, 2019

(54) TREATMENT AGENT FOR COGNITIVE IMPAIRMENT INDUCED BY AMYLOID BETA-PROTEIN, THERAPEUTIC AGENT FOR ALZHEIMER'S DISEASE, AND TREATMENT METHOD AND PATHOLOGICAL ANALYSIS METHOD RELATED TO THESE

(71) Applicants: NATIONAL UNIVERSITY CORPORATION OKAYAMA UNIVERSITY, Okayama-Shi, Okayama (JP); NATIONAL UNIVERSITY CORPORATION HOKKAIDO UNIVERSITY, Sapporo-Shi, Hokkaido (JP)

(72) Inventors: Tsuyoshi Inoue, Okayama (JP); Toshiharu Suzuki, Sapporo (JP); Saori Ban, Sapporo (JP)

(73) Assignees: NATIONAL UNIVERSITY CORPORATION OKAYAMA UNIVERSITY, Okayama-Shi (JP); NATIONAL UNIVERSITY CORPORATION HOKKAIDO UNIVERSITY, Sapporo-Shi (JP)

( * ) Notice: Subject to any disclaimer, the term of this patent is extended or adjusted under 35 U.S.C. 154(b) by 0 days.

(21) Appl. No.: 15/725,357

(22) Filed: Oct. 5, 2017

(65) Prior Publication Data
US 2018/0036372 A1 Feb. 8, 2018

Related U.S. Application Data

(62) Division of application No. 14/785,204, filed as application No. PCT/JP2014/060665 on Apr. 15, 2014, now abandoned.

(30) Foreign Application Priority Data

Apr. 19, 2013 (JP) .................................. 2013-088319

(51) Int. Cl.
| | |
|---|---|
| A61K 38/17 | (2006.01) |
| A61K 38/08 | (2006.01) |
| C07K 7/06 | (2006.01) |
| C07K 7/08 | (2006.01) |
| A61K 38/00 | (2006.01) |
| C07K 14/47 | (2006.01) |

(52) U.S. Cl.
CPC .......... *A61K 38/1709* (2013.01); *A61K 38/00* (2013.01); *C07K 14/4711* (2013.01); *C07K 7/06* (2013.01); *C07K 7/08* (2013.01)

(58) Field of Classification Search
CPC .......................... A61K 38/00; A61K 38/1709; C07K 14/4711; C07K 7/06; C07K 7/08; C07K 14/47
See application file for complete search history.

(56) References Cited

U.S. PATENT DOCUMENTS

| | | | |
|---|---|---|---|
| 3,391,142 | A | 7/1968 | Mills et al. |
| 4,895,841 | A | 1/1990 | Sugimoto et al. |
| 5,100,901 | A | 3/1992 | Sugimoto et al. |
| 7,666,982 | B2 | 2/2010 | Okochi et al. |
| 7,807,777 | B2 | 10/2010 | Suzuki et al. |
| 2004/0077627 | A1 | 4/2004 | Koenig et al. |
| 2004/0198778 | A1 | 10/2004 | Kreft et al. |
| 2004/0248878 | A1 | 12/2004 | Koenig et al. |
| 2005/0261495 | A1 | 11/2005 | Audia et al. |
| 2007/0299053 | A1 | 12/2007 | Audia et al. |
| 2010/0221187 | A1 | 9/2010 | Lieberburg et al. |
| 2010/0323375 | A1 | 12/2010 | Maeda et al. |
| 2011/0014635 | A1 | 1/2011 | Suzuki et al. |
| 2011/0229413 | A1 | 9/2011 | Lieberburg et al. |

FOREIGN PATENT DOCUMENTS

| | | | | |
|---|---|---|---|---|
| EP | 0296560 A2 | 12/1988 | | |
| WO | WO-0222819 A2 | * 3/2002 | ......... | C07K 14/4728 |
| WO | 02/40451 A2 | 5/2002 | | |
| WO | 2009/017467 A1 | 2/2009 | | |
| WO | 2009/075084 A1 | 6/2009 | | |
| WO | 2012/137502 A1 | 10/2012 | | |

OTHER PUBLICATIONS

Uchida Y et al. Up-regulation of calsyntenin-3 by beta-amyloid increase vulnerability of cortical neurons. FEBS Lett. 2011, 585:651-656. (Year: 2011).*

International Search Report dated Jul. 1, 2014, issued in counterpart application No. PCT/JP2014/060665. (2 pages).

De Strooper, et al., "The secretases: enzymes with therapeutic potential in Alzheimer disease", Nat Rev Neurol, Feb. 2010, vol. 6, No. 2, pp. 99-107.

Lambert, et al., "Diffusible, nonfibrillar ligands derived from Abeta1-42 are potent central nervous system neurotoxins" Proc. Natl. Acad. Sci. USA, May 1998, vol. 95, pp. 6448-6453.

(Continued)

*Primary Examiner* — Kimberly Ballard
(74) *Attorney, Agent, or Firm* — Westerman, Hattori, Daniels & Adrian, LLP (57) ABSTRACT

Disclosed is a method of treatment for anti-Alzheimer's disease based on an action mechanism associated with amyloid β protein, which action mechanism is different from conventional action mechanisms. The treatment Alzheimer's disease uses a therapeutic agent for cognitive impairment induced by amyloid β protein, which therapeutic agent comprises a peptide having the amino acid sequence represented by SEQ ID NO:1 or a peptide similar to this peptide, especially a peptide containing the amino acid sequence represented by SEQ ID NO:2, which is a partial sequence of SEQ ID NO:1. VLSSQQFLHRGHQPPPEMAGHS-LASSHRNSMIPSAAT (SEQ ID NO:1) HRGHQPPPEMA (SEQ ID NO:2).

1 Claim, 3 Drawing Sheets

Specification includes a Sequence Listing.

(56) References Cited

OTHER PUBLICATIONS

Walsh, et al., "Naturally secreted oligomers of amyloid beta protein potently inhibit hippocampal long-term potentiation in vivo", Nature, Apr. 4, 2002, vol. 416, pp. 535-539.
Cleary, et al., "Natural oligomers of the amyloid-beta protein specifically disrupt cognitive function" Nature Neuroscience, Jan. 2005, vol. 8, No. 1, pp. 79-84.
Balducci, et al., "Synthetic amyloid-beta oligomers impair long-term memory independently of cellular prion protein" Proc Natl Acad Sci, Feb. 2, 2010, vol. 107, No. 5, pp. 2295-2300.
Brouillette, et al., "Neurotoxicity and Memory Deficits Induced by Soluble Low-Molecular-Weight Amyloid-beta1-42 Oligomers Are Revealed In Vivo by Using a Novel Animal Model", The Journal of Neuroscience, Jun. 6, 2012, vol. 32, No. 23, pp. 7852-7861.
Haapasalo, et al., "The Many Substrates of Presenilin/gamma-Secretase", J Alzheimers Dis, 2011, vol. 25, No. 1, pp. 3-28.
De Strooper, et al.,"A presenilin-1-dependent gamma-secretase-like protease mediates release of Notch intracellular domain" Nature, Apr. 8, 1999, vol. 398, pp. 518-522.
Okochi, et al., "Presenilins mediate a dual intramembranous gamma-secretase cleavage of Notch-1", The EMBO Journal, 2002, vol. 21, No. 20, pp. 5408-5416.
Araki, et al., "Coordinated Metabolism of Alcadein and Amyloid Beta-Protein Precursor Regulates FE65-dependent Gene Transactivation", The Journal of Biological Chemistry, 2004, vol. 279, No. 23, pp. 24343-24354.
Hata, et al., "Alcadein Cleavages by Amyloid beta-Precursor Protein (APP) alpha- and gamma-Secretases Generate Small Peptides, p3-Alcs, Indicating Alzheimer Disease-related gamma-Secretase Dysfunction", Journal of Biological Chemistry, Dec. 25, 2009, vol. 284, No. 52, pp. 36024-36033.
Rampon, et al., "Enrichment induces structural changes and recovery from nonspatial memory deficits in CA1 NMDAR1-knockout mice", Nature Neuroscience, Mar. 2000, vol. 3, No. 3, pp. 238-244.
De Lima, et al., "Pre- or post-training administration of the NMDA receptor blocker MK-801 impairs object recognition memory in rats", Behavioural Brain Research, 2005, vol. 156, pp. 139-143.
Araki, et al., Novel Cadherin-related Membrane Proteins, Alcadeins, Enhance the X11-like protein-mediated stabilization of Amyloid beta-Protein Precursor Metabolism, Journal of Biological Chemistry, Dec. 5, 2003, vol. 278, No. 49, pp. 49448-49458.
Mizumaru, et al., "Suppression of APP-containing vesicle trafficking and production of beta-amyloid by AID/DHHC-12 protein", Journal of Neurochemistry, 2009, vol. 111, No. 5, pp. 1213-1224.
Hata, et al., "Alcadein to gamma-secretase", Brain 21, 2012, vol. 15, No. 4, pp. 449-453, w/partial English translation.
Amino acid sequence for Calsyntenin-3 precursor [Bos taurus], NCBI reference sequence NP_001068893.2, PubMed Protein, retrieved from internet Jun. 29, 2017, pp. 1 and 2.

* cited by examiner

SEQUENCE LISTING

```
<160> NUMBER OF SEQ ID NOS: 6

<210> SEQ ID NO 1
<211> LENGTH: 37
<212> TYPE: PRT
<213> ORGANISM: Homo sapiens

<400> SEQUENCE: 1

Val Leu Ser Ser Gln Gln Phe Leu His Arg Gly His Gln Pro Pro Pro
1               5                   10                  15

Glu Met Ala Gly His Ser Leu Ala Ser Ser His Arg Asn Ser Met Ile
            20                  25                  30

Pro Ser Ala Ala Thr
        35

<210> SEQ ID NO 2
<211> LENGTH: 11
<212> TYPE: PRT
<213> ORGANISM: Artificial Sequence
<220> FEATURE:
<223> OTHER INFORMATION: a part of p3-Alc beta 37 (position 9-19)
```

```
<400> SEQUENCE: 2

His Arg Gly His Gln Pro Pro Glu Met Ala
1               5                   10

<210> SEQ ID NO 3
<211> LENGTH: 11
<212> TYPE: PRT
<213> ORGANISM: Artificial Sequence
<220> FEATURE:
<223> OTHER INFORMATION: a part of p3-Alc beta 37 (position 1-11)

<400> SEQUENCE: 3

Val Leu Ser Ser Gln Gln Phe Leu His Arg Gly
1               5                   10

<210> SEQ ID NO 4
<211> LENGTH: 19
<212> TYPE: PRT
<213> ORGANISM: Artificial Sequence
<220> FEATURE:
<223> OTHER INFORMATION: a part of p3-Alc beta 37 (position 1-19)

<400> SEQUENCE: 4

Val Leu Ser Ser Gln Gln Phe Leu His Arg Gly His Gln Pro Pro
1               5                   10                  15

Glu Met Ala

<210> SEQ ID NO 5
<211> LENGTH: 18
<212> TYPE: PRT
<213> ORGANISM: Artificial Sequence
<220> FEATURE:
<223> OTHER INFORMATION: a part of p3-Alc beta 37 (position 20-37)

<400> SEQUENCE: 5

Gly His Ser Leu Ala Ser Ser His Arg Asn Ser Met Ile Pro Ser Ala
1               5                   10                  15

Ala Thr

<210> SEQ ID NO 6
<211> LENGTH: 42
<212> TYPE: PRT
<213> ORGANISM: Homo sapiens

<400> SEQUENCE: 6

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

TREATMENT AGENT FOR COGNITIVE IMPAIRMENT INDUCED BY AMYLOID BETA-PROTEIN, THERAPEUTIC AGENT FOR ALZHEIMER'S DISEASE, AND TREATMENT METHOD AND PATHOLOGICAL ANALYSIS METHOD RELATED TO THESE

CROSS-REFERENCE TO RELATED APPLICATION

This application is a Divisional of copending U.S. patent application Ser.No. 14/785,204, filed on Oct. 16, 2015, which is a U.S. National Stage entry of International Application No. PCT/JP2014/060665, filed on Apr. 15, 2014, which claims priority to Japanese Patent Application No. 2013-088319, filed on Apr. 19, 2013, the entirety of which is incorporated herein by reference.

TECHNICAL FIELD

The present invention relates to a peptide having a therapeutic effect on cognitive impairment induced by amyloid β protein, which is a symptom of Alzheimer's disease, and use of the peptide.

BACKGROUND ART

Alzheimer's disease is a nervous disease which exhibits a decline in cognitive function (for example, memory disorder) as a main symptom. Although Alzheimer's disease frequently develops in the elderly, there is not effective therapeutic drug, and this has become a big problem in developed countries in which the society is aging. In postmortem brains of patients with Alzheimer's disease, senile plaques are found. These are known to be aggregates of "amyloid β protein". The fact that amyloid βprotein is the main cause of Alzheimer's disease is widely accepted based on a number of studies.

Amyloid β protein is produced from its precursor, "amyloid precursor protein". Amyloid precursor protein is a membrane protein present on the nerve cell membrane. In normal brain, cleavage of the extracellular domain of amyloid precursor protein with α-secretase followed by cleavage of the domain inside the cell membrane with γ-secretase causes production and extracellular release of a peptide called p3. This is called "non-amyloidogenic pathway", and amyloid β protein is not produced in the pathway (Non-patent Document 1). In normal brain, only several percent of the extracellular domain undergoes cleavage by β-secretase, to cause extracellular secretion of amyloid β protein. On the other hand, it has been thought that the brain of a patient developing Alzheimer's disease exhibits increased production of amyloid β protein, or production of a molecular species of amyloid β protein having higher aggregability. Due to the property of amyloid β protein to cause aggregation, senile plaques (amyloid aggregates) are finally formed in patients with Alzheimer's disease, and these senile plaques are found as deposition in the brain.

After being cleaved out, amyloid β protein gradually aggregates to finally form senile plaques (amyloid aggregates). The "oligomer (which is composed of several amyloid β protein units associated with each other)" produced during the aggregation process is known to have strong neurotoxicity. From both in vitro and in vivo studies, the oligomer of amyloid β protein is reported to inhibit synaptic plasticity, which is a neurological phenomenon indispensable for memory and learning (Non-patent Documents 2 and 3) it is also reported that administration of the oligomer into the brain of a mouse causes loss of memory and learning ability (Non-patent Documents 4 and 5). A recent study also reported that long-term exposure to the oligomer causes neuronal death and the like (Non-patent Document 6). The oligomer is therefore attracting attention as a causative substance for development of Alzheimer's disease.

Thus, in spite of the fact that amyloid β protein is widely recognized as a cause of Alzheimer's disease, the therapeutic drugs for Alzheimer's disease that are clinically used at present are not designed such that they act on amyloid β protein. More specifically, donepezil (Patent Document 1) and memantine (Patent Document 2), which are used as therapeutic drugs for Alzheimer's disease, act as an acetylcholine esterase inhibitor and an NMDA receptor inhibitor, respectively, and do not interact with amyloid β protein. Since these are the so called symptomatic drugs, they have no drastic action to ameliorate Alzheimer's disease at present.

Under such circumstances, development of novel therapeutic drugs for Alzheimer's disease based on the action mechanism (associated with amyloid protein) is in progress. In an attempt to suppress production of amyloid β protein from amyloid precursor protein, secretase regulating agents are being developed (Non-patent Document 1). In particular, development of γ-secretase inhibitors is most rapidly progressing, and Semagacestat (Patent Document 3), Begacestat (Patent Document 4), and the like have been clinically developed one after another. Another therapeutic method which is drawing attention is an antibody therapy based on recognition and elimination of amyloid β protein in the brain by an antibody. Bapineuzumab (Patent Document 5), solanezumab, and the like have been actually clinically developed so far.

However, the therapeutic drugs for Alzheimer's disease having action mechanisms associated with amyloid protein which are mainly developed at present are known to have problems. In terms of γ-secretase inhibitors, it is known that the substrate for γ-secretase is originally not limited to amyloid precursor protein, and that there are about 100 kinds of its substrates (Non-patent Document 7). Since the Notch receptor, which is important for cell differentiation, is included in such substrates (Non-patent Document 8), there is a concern that side effects may occur. Actually, development of Semagacestat, which had been a major candidate for a γ-secretase inhibitor, was stopped after the phase III clinical trial in 2010. The antibody therapy using an anti-amyloid β antibody may cause angiitis, vasogenic cerebral edema, and/or the like. Actually, development of Bapineuzumab, which had been a promising agent for antibody therapy, was stopped in 2012.

Some γ-secretase substrates are known to release their extracellular domains after cleavage, similarly to the amyloid peptide (Non-patent Documents 9 and 10). Since these peptides can be used as indices of γ-secretase, there are several inventions that attempt to use the cleaved fragments as biomarkers for Alzheimer's disease (Patent Documents 6 and 7). It is also known that the membrane protein called Alcadein -β in the living body is cleaved both by γ-secretase and by α-secretase, resulting in production of a peptide composed of 37 amino acids (VLSSQQFLHRGHQP-PPEMAGHSLASSHRNSMIPSAAT) (Non-patent Document 11).

However, an idea to use such a peptide as a regulating agent for Alzheimer's disease is difficult to expect under the current levels of knowledge and technology, and, accordingly, there has been no report on such an idea.

PRIOR ART DOCUMENTS

Patent Documents

[Patent Document 1] EP 0296560 A2
[Patent Document 2] U.S. Pat. No. 3,391,142 A
[Patent Document 3] WO 2002/40451 A2
[Patent Document 4] US 2004/198778 A1
[Patent Document 5] WO 2009/017467 A1
[Patent Document 6] U.S. Pat. No. 7,666,982 B2
[Patent Document 7] U.S. Pat. No. 7,807,777 B2

Non-Patent Documents

[Non-patent Document 1] De Strooper et al., Nat Rev Neurol 6, 99-107, 2010
[Non-patent Document 2] Lambert et al., Proc Natl Acad Sci USA 95, 6448-6453, 1998
[Non-patent Document 3] Walsh et al., Nature 416, 535-539, 2002
[Non-patent Document 4] Cleary et al., Nat Neurosci 8, 79-84, 2005
[Non-patent Document 5] Balducci et al., Proc Nati Acad Sci USA 107, 2295-2300, 2010
[Non-patent Document 6] Brouillette et al., J Neurosci 32, 7852-7861, 2012
[Non-patent Document 7] Haapasalo and Kovacs, J Alzheimers Dis 25, 3-28, 2011
[Non-patent Document 8] De Strooper et al., Nature 398, 518-522, 1999
[Non-patent Document 9] Okochi et al., EMBO J 21, 5408-5416, 2002
[Non-patent Document 10] Araki et al., J Biol Chem 279, 24343-24354, 2004
[Non-patent Document 11] Hata et al., J Biol Chem 284, 36024-36033, 2009

SUMMARY OF THE INVENTION

Problems to be Solved by the Invention

Under the circumstances described above, an anti-Alzheimer's disease agent based on an action mechanism associated with amyloid β protein, which action mechanism is different from conventional action mechanisms, has been demanded, and the present invention aims to provide such an anti-Alzheimer's disease agent.

Means for Solving the Problems

As described above, γ-secretase is known to cleave membrane proteins other than amyloid precursor protein. The present inventors made a daring hypothesis that peptide fragments themselves "other than" the amyloid β protein, produced by cleavage by γ-secretase might exhibit actions to ameliorate Alzheimer's disease. In view of this, the present inventors discovered that, among such peptide fragments, the above-described peptide composed of 37 amino acids (VLSSQQFLHRGHQPPPEMAGHSLASSHRNSMIPSAAT) produced by cleavage of Alcadein-β both by γ-secretase and by α-secretase (p3-Alcβ37 peptide) drastically ameliorates cognitive impairment due to amyloid β protein, and that even a peptide composed of only 11 amino acids (HRGHQPPPEMA) contained in the p3-Alcβ37 peptide (p3-Alcβ[9-19] peptide) has the action to ameliorate cognitive impairment, thereby completing the present invention.

That is, in one aspect of the present invention, a therapeutic agent for cognitive impairment induced by amyloid β protein and a therapeutic drug for Alzheimer's disease are provided. In another aspect of the present invention, a method for treatment of cognitive impairment induced by amyloid β protein and a method for treatment of Alzheimer's disease are provided. In still another aspect of the present invention, a method for pathological analysis of cognitive impairment induced by amyloid β protein and a method for pathological analysis of Alzheimer's disease are provided. These present inventions include the following inventions.

[1] A therapeutic agent for cognitive impairment induced by amyloid β protein, comprising as an effective component a peptide corresponding to any one of the following (I) to (VI):

(I) a peptide consisting of the amino acid sequence represented by SEQ ID NO:1:
VLSSQQFLHRGHQPPPEMAGHSLASSHRNSMIPSAAT (SEQ ID NO:1);

(II) a peptide consisting of the same amino acid sequence as the amino acid sequence represented by SEQ ID NO:1 except that one to three amino acids are altered by any one or more of deletion, addition, substitution, and side-chain modification;

(III) a peptide consisting of a partial sequence of the amino acid sequence represented by SEQ ID NO:1, comprising the amino acid sequence represented by SEQ ID NO:2:
HRGHQPPPEMA (SEQ ID NO: 2);

(IV) a peptide consisting of the same amino acid sequence as a partial sequence of the amino acid sequence represented by SEQ ID NO: 1 comprising the amino acid sequence represented by SEQ ID NO:2, except that one or two amino acids are altered by any one or more of deletion, addition, substitution, and side-chain modification;

(V) a peptide consisting of an amino acid sequence comprising the amino acid sequence represented by SEQ ID NO:2, wherein a total of 1 to 50 amino acids are added to the N-terminus and/or the C-terminus of the amino acid sequence represented by SEQ ID NO:2 (excluding amino acid sequences which are identical to all or part of the amino acid sequence represented by SEQ ID NO:1); and (VI) a peptide consisting of an amino acid sequence comprising the same amino acid sequence as the amino acid sequence represented by SEQ ID NO:2 except that one or two amino acids are altered by any One or more of deletion, addition (excluding addition to the N-terminus and/or the C-terminus), substitution, and side-chain modification, wherein a total of 1 to 50 amino acids are added to the N-terminus and/or the C-terminus of the altered amino acid sequence.

[2] A therapeutic drug for Alzheimer's disease, comprising the therapeutic agent according to [1].

[3] A method for treatment of cognitive impairment induced by amyloid β protein, comprising a step of administering the therapeutic agent according to [1] to a mammal (excluding human) which developed cognitive impairment induced by amyloid β protein or to a model animal thereof.

[4] A method for treatment of Alzheimer's disease, comprising a step of administering the therapeutic drug according to [2] to a mammal (excluding human) which developed Alzheimer's disease or to a model animal thereof.

[5] A method for pathological analysis of cognitive impairment induced by amyloid β protein, comprising a step of administering a peptide corresponding to any one of the above (I) to (VI) to a mammal (excluding human) which developed cognitive impairment induced by amyloid β protein or to a model animal thereof, or a step of adding the peptide to a cultured nerve cell (s) as a model cell(s) thereof or to a biomolecule(s) expressed in a nerve cell(s).

[6] A method for pathological analysis of Alzheimer's disease, comprising a step of administering a peptide corresponding to any one of the above (I) to (VI) to a mammal (excluding human) which developed Alzheimer's disease or to a model animal thereof, or a step of adding the peptide to a cultured nerve cell (s) as a model cell(s) thereof or to a biomolecules) expressed in a nerve cell(s).

It is evident to those skilled in the art that the above-described inventions can be converted to inventions represented as, for example, use of the specific peptide as an effective component of a therapeutic agent for cognitive impairment induced by amyloid β protein or a therapeutic drug for Alzheimer's disease (in production of these agents).

EFFECT OF THE INVENTION

Since there is no effective therapeutic drug for Alzheimer's disease at present, a novel therapeutic drug is demanded. As described in Background Art, novel therapeutic drugs based on amyloid β protein are being clinically developed, but they are still commercially unavailable because of their side effects and the like. The anti-Alzheimer's disease agent provided by the present invention has a novel action mechanism that is different from those of conventional anti-Alzheimer's disease agents, and uses a peptide which is produced by cleavage by γ-secretase and actually present in the living body (p3-Alcβ37) per se or a partial peptide thereof (p3-Alcβ[9-19]), or a peptide having an amino acid sequence similar to these peptides, so that the agent can be an anti-Alzheimer' s disease agent which has no side effect and whose high safety can be expected.

BRIEF DESCRIPTION OF THE DRAWINGS

Discrimination index=([exploration time for novel object]−[exploration time for familiar object])/ ([exploration time for novel object]+[exploration time for familiar object]).

**:P<0.01.

FIG. 4 shows the effects of partial p3-Alcβ37 (SEQ ID NO: 1)peptides on memory disorder induced by an amyloid β protein oligomer. A: Comparison of the amino acid sequence among the following partial peptides used in the experiment: p3-Alcβ[1-19], p3-Alcβ[20-37], p3-Alcβ[1-11],and p3-Alcβ[9-19]. B (Aβ oligomer+p3-Alcβ[1-19]): Artificial cerebrospinal fluid in which 1 μM amyloid β protein oligomer and 10 μM p3-Alcβ[1-19] peptide are dissolved. :P<0.01. C (Aβ oligomer+p3-Alcβ[20-37]): Artificial cerebrospinal fluid in which 1 μM amyloid β protein oligomer and 10 μM p3-Alcβ[20-37] peptide are dissolved. D (Aβ oligomer+p3-Alcβ[1-11]): Artificial cerebrospinal fluid in which 1 μM amyloid β protein oligomer and 10 μM p3-Alcβ[1-11] peptide are dissolved. E (Aβ oligomer+p3-Alcβ[9-19]): Artificial cerebrospinal fluid in which 1 μM amyloid β protein oligomer and 10 μM p3-Alcβ [9-19] peptide are dissolved. :P<0.01.

MODE FOR CARRYING OUT THE INVENTION

—Therapeutic Agent—

The therapeutic agent for cognitive impairment induced by amyloid β protein according to the present invention includes the first to sixth embodiments described below.

The "amyloid β protein" herein is a polypeptide generally known to accumulate in the brain as Alzheimer's disease progresses, and may be in any of the form of a monomer composed of a single polypeptide chain, the form of an oligomer composed of several (usually, 2 to 6) polypeptide chains, and the form of an aggregate composed of a plurality of such oligomers. The "cognitive impairment induced by amyloid β protein" includes memory disorder, disorientation, learning disability, disturbance of attention, and disorders of spatial cognitive function and problem-solving abilities, which are generally known as symptoms of Alzheimer's disease.

In the first embodiment, a peptide consisting of the amino acid sequence represented by SEQ ID NO:1 is used as an effective component of the therapeutic agent of the present invention.

VLSSQQFLHRGHQPPPEMAGHSLASSHRNSMIPSAAT (SEQ ID NO: 1)

In the second embodiment, a peptide consisting of the same amino acid sequence as the amino acid sequence represented by SEQ ID NO:1 except that one to three amino acids are altered by any one or more of deletion, addition, substitution, and side-chain modification (corresponding to a non-natural amino acid, post-translationally modified amino acid, or the like) is used as an effective component of the therapeutic agent of the present invention. The deletion includes not only deletions at the N-terminus and/or the C-terminus of the amino acid sequence represented by SEQ ID NO:1, but also deletions inside the amino acid sequence represented by SEQ ID NO:1. The addition includes not only additions at the N-terminus and/or the C-terminus of the amino acid sequence represented by SEQ ID NO: 1, but also additions inside, that is, insertions into, the amino acid sequence represented by SEQ ID NO: 1 . In the second embodiment, the number of the amino acids that are altered is usually 1 to 3, preferably 1 to 2, more preferably 1. In cases where the amino acid sequence is altered by a combination of two or more of deletion, addition, substitution, and side-chain modification, the number described above indicates their total number. As long as the action and effect of the present invention are not deteriorated, such deletion, addition (insertion), substitution, and/or side-chain modification in the second embodiment may be carried out either in the part corresponding to the amino acid sequence represented by SEQ ID NO:2 (HRGHQPPPEMA) contained in the amino acid sequence represented by SEQ ID NO:1, or in a part other than the amino acid sequence represented by SEQ ID NO:2.

In the third embodiment, a peptide consisting of a partial sequence of the amino acid sequence represented by SEQ ID NO:1, especially a peptide consisting of a partial sequence comprising the amino acid sequence represented by SEQ ID NO:2, is used as an effective component of the therapeutic agent of the present invention.
HRGHQPPPEMA (SEQ ID NO:2)

Here, the partial sequence is a partial continuous amino acid sequence in the amino acid sequence represented by SEQ ID NO:1 (that is, the entire amino acid sequence represented by SEQ ID NO:1 is not included in the definition of "partial sequence"), and can be prepared by removing at least one amino acid from the N-terminus and/or the C-terminus of a peptide consisting of the amino acid sequence represented by SEQ ID NO:1. Such a peptide having the partial sequence may be a peptide consisting of only the amino acid sequence represented by SEQ ID NO:2, or may be a peptide consisting of an amino acid sequence in which an amino acid sequence(s) is/are added to the N-terminus and/or the C-terminus of the amino acid sequence represented by SEQ ID NO:2 correspondingly to SEQ ID NO:1.

It should be noted that the peptides used in the third embodiment may overlap with (have the same meaning as) the peptides used in the second embodiment. For example, amino acid sequences which are the same as the amino acid sequence represented by SEQ ID NO:1 (37 amino acids in length) except that a total of 1 to 3 amino acids at the N-terminus and/or the C-terminus are deleted (34 to 36 amino acids in length), which are used in the second embodiment, may overlap with amino acid sequences which are the same as the amino acid sequence represented by SEQ ID NO:2 (11 amino acids in length) except that a total of 23 to 25 amino acids are added to the N-terminus and/or the C-terminus (34 to 36 amino acids in length). If necessary, the peptides used in the third embodiment may be defined such that the peptides used in the second embodiment are excluded. This also applies to the peptides used in the fourth embodiment.

In the fourth embodiment, a peptide consisting of the same amino acid sequence as a partial sequence of the amino acid sequence represented by SEQ ID NO:1, especially a partial sequence comprising the amino acid sequence represented by SEQ ID NO:2 (that is, the partial sequence defined in the third embodiment), except that one or two amino acids are altered by any one or more of deletion, addition, substitution, and side-chain modification, is used as an effective component of the therapeutic agent of the present invention. The deletion includes not only deletions at the N-terminus and/or the C-terminus of the partial sequence of the amino acid sequence represented by SEQ ID NO:1, but also deletions inside the amino acid sequence represented by SEQ ID NO:1. The addition includes not only additions at the N-terminus and/or the C-terminus of the partial sequence of the amino acid sequence represented by SEQ ID NO:1, but also additions inside, that is, insertions into, the partial sequence. In the fourth embodiment, the number of the amino acids that are altered is usually 1 to 2, preferably 1. In cases where the amino acid sequence is altered by a combination of two or more of deletion, addition, substitution, and side-chain modification, the number described above indicates their total number. As long as the action and effect of the present invention are not deteriorated, such deletion, addition (insertion), substitution, and/or side-chain modification in the fourth embodiment may be carried out either in the part corresponding to the amino acid sequence represented by SEQ ID NO:2 (HRGHQPPPEMA), or in a part other than the amino acid sequence represented by SEQ ID NO:2.

In the fifth embodiment, a peptide consisting of an amino acid sequence comprising the amino acid sequence represented by SEQ ID NO:2, Wherein a total of 1 to 50 amino acids are added to the N-terminus and/or the C-terminus of the amino acid sequence represented by SEQ ID NO:2, is used as an effective component of the therapeutic agent of the present invention. The number of the amino acids added in the fifth embodiment is usually 1 to 50, preferably 1 to 26 (this corresponds to a total peptide length of up to 37 after the addition, which is the same as the length of p3-Alcβ37), more preferably 1 to 8 (this corresponds to a total peptide length of up to 19 after the addition, which is the same as the length of p3-Alcβ[1-19]).

It should be noted that the peptides used in the fifth embodiment may overlap with (have the same meaning as) the peptides used in the first to fourth embodiments. For example, the amino acid sequence represented by SEQ ID NO: 1 (37 amino acids in length) which is used in the first embodiment, can also be said to be an amino acid sequence comprising the amino acid sequence represented by SEQ ID NO:2 (11 amino acids in length; the 9th to 19th amino acids in SEQ ID NO:1), wherein 9 amino acids (the 1st to 8th amino acids in SEQ ID NO:1) are added to the N-terminus and 18 amino acids (the 20th to 37th amino acids in SEQ ID NO:1) are added to the C-terminus of the amino acid sequence represented by SEQ ID NO:2. If necessary, the peptides used in the fifth embodiment maybe defined such that the peptides used in the first to fourth embodiment are excluded. This also applies to the peptides used in the sixth embodiment described below.

In the sixth embodiment, a peptide consisting of an amino acid sequence comprising the same amino acid sequence as the amino acid sequence represented by SEQ ID NO:2 except that one or two amino acids are altered by any one or more of deletion, addition, substitution, and side-chain modification, wherein a total of 1 to 50 amino acids are added to the N-terminus and/or the C-terminus of the altered amino acid sequence, is used as an effective component of the therapeutic agent of the present invention. The deletion includes not only deletions at the N-terminus and/or the C-terminus of the amino acid sequence represented by SEQ ID NO:2, but also deletions inside the amino acid sequence represented by SEQ ID NO:2. The addition includes not only additions at the N-terminus and/or the C-terminus of the amino acid sequence represented by SEQ ID NO:2 (in this case, the addition of "1 to 50" amino acids described in the latter half of the recitation of the sixth embodiment may be carried out in addition to the addition of "one or two" amino acids described in the first half of the recitation), but also additions inside, that is, insertions into, the partial sequence. In the sixth embodiment, the number of the amino acids that are further added to the N-terminus and/or the C-terminus of the altered amino acid sequence is usually 1 to 50, preferably 1 to 26 (this corresponds to a total peptide length of up to 37 after the addition, which is the same as the length of p3-Alcβ37; however, in cases where one or two amino acids are deleted from or added to the amino acid sequence represented by SEQ ID NO:2, the decrease or increase in the number of amino acids due to the deletion or addition may be taken into account), more preferably 1 to 8 (this corresponds to a total peptide length of up to 19 after the addition, which is the same as the length of p3-Alcβ[1-19]; however, in cases where one or two amino acids are deleted from or added to the amino acid sequence represented by SEQ ID NO:2, the decrease or increase in the number of amino acids due to the deletion or addition may be taken into account)

Those skilled in the art can select, without requiring excessive trial and error, a peptide that exerts the action and effect to treat cognitive impairment induced by amyloid β protein among the peptides having the amino acid sequences defined in the second to sixth embodiments, and use the selected peptide in the present invention.

The peptides used in the first to sixth embodiments can be prepared by a known method, and the method of preparation is not limited. For example, a peptide consisting of a desired amino acid sequence can be prepared by sequentially linking amino acids using the Fmoc-peptide solid-phase synthesis, which is a conventionally used method for peptide synthesis.

The therapeutic agent according to the present invention described above, or the predetermined peptide contained therein, can be suitably used as an effective component of therapeutic drugs for Alzheimer's disease. However, the embodiment of the therapeutic agent according to the present invention or the predetermined peptide contained therein is not limited to the uses for such drugs (pharmaceuticals). For example, the therapeutic agent according to the present invention or the predetermined peptide contained therein may be used in an embodiment in which the therapeutic agent or the predetermined peptide is administered to the body of human or a mammal other than human who developed cognitive impairment induced by amyloid β protein, or a model animal thereof (e.g., mouse, rat, guinea pig, rabbit, goat, cat, dog, pig, or monkey) to allow the therapeutic agent or the predetermined peptide to act in vivo in order to study details of its therapeutic effect on the cognitive impairment or its action mechanism, or an embodiment in which the therapeutic agent or the predetermined peptide is added to model cells prepared from cultured nerve cells derived from any of these animals to allow the therapeutic agent or the predetermined peptide to act in vitro.

The therapeutic agent according to the present invention may be prepared as an agent containing only a predetermined peptide as an effective component, and the peptide alone or a solution of the peptide in an appropriate solvent (for example, artificial cerebrospinal fluid) may be used for the administration or the addition. Alternatively, the therapeutic agent according to the present invention may be prepared as a formulation according to the therapeutic drug described below, to be used for the administration or the addition.

—Therapeutic Drug—

The therapeutic drug for Alzheimer's disease according to the present invention contains the therapeutic agent according to the present invention, and may optionally contain, for example, an effective component other than the therapeutic agent (predetermined peptide) of the present invention, a pharmaceutically acceptable carrier suitable for the dosage form, and/or other pharmaceutical additives used for common pharmaceuticals. That is, the therapeutic drug for Alzheimer's disease according to the present invention may be prepared as a pharmaceutical composition containing such a component(s).

Examples of the dosage form of the therapeutic drug which may be selected include dosage forms for oral administration, such as tablets, capsules, soft capsules, granules, powders, fine granules, (dry) syrups, solutions, and suspensions; and dosage forms for parenteral administration, such as injections for subcutaneous, intramuscular, or intravenous administration, drops, suppositories, and transnasal agents.

The pharmaceutical compositions having such dosage forms can be produced by common production methods. For example, a dosage form for oral administration can be produced by mixing the effective component with one or more of additives such as Vehicles, disintegrators, binders, lubricants, suspending agents, isotonic agents, emulsifiers, sweeteners, flavoring agents, and coloring agents by a conventional method, and molding the resulting mixture. Examples of the vehicles include cellulose derivatives (for example, crystalline cellulose, methylcellulose, hydroxypropyl cellulose, and hydroxypropyl methyl cellulose); polyvinylpyrrolidone; dextrin; starch; lactose; mannitol; sorbitol; vegetable oils (for example, corn oil, cottonseed oil, coconut oil, almond oil, olive oil, and peanut oil); oily esters such as medium-chain fatty acid glyceride oils; mineral oil; glycerin esters such as tricaprilin and triacetin; alcohols such as ethanol; physiological saline; propylene glycol; polyethylene glycol; animal fats and oils; and vaseline.

The injection can be produced by dissolving the effective component in an appropriate diluent (physiological saline, glucose injection, lactose injection, mannitol injection, or the like) and subjecting the resulting solution to sterilization treatment such as sterilization by filtration, followed by filling the sterilized solution into a sealable container such as an ampule. Alternatively, the injection can be produced in the form of a product freeze-dried according to the Japanese Pharmacopoeia, or as a powder for injection prepared by mixing with sodium chloride. As the additive, an adjuvant such as polyethylene glycol or a surfactant.; or a carrier such as ethanol, liposome, or cyclodextrine; may be used.

The content of the effective component in the pharmaceutical composition may be controlled within an appropriate range. The content of the effective component is usually 0.05 to 99 wt %, preferably 0.1 to 70 wt %, more preferably 0.1 to 50 wt % with respect to the total weight of the pharmaceutical composition.

—Therapeutic Method—

The therapeutic agent described above may be used for treating cognitive impairment induced by amyloid β protein. The therapeutic drug described above may be used for treating Alzheimer' s disease.

That is, the method for treatment of cognitive impairment induced by amyloid β protein according to the present invention comprises a step of administration to a mammal (human, or a mammal other than human) which developed cognitive impairment induced by amyloid β protein or to a model animal (a mammal other than human) thereof. The method for treatment of Alzheimer's disease according to the present invention comprises a step of administration to a mammal (excluding human) which developed Alzheimer's disease or to a model animal thereof.

The cognitive impairment induced by amyloid β protein to be treated with the therapeutic agent according to the present invention typically means symptoms accompanying Alzheimer's disease, but may be symptoms accompanying a disease which has not been definitively diagnosed with Alzheimer's disease, or symptoms in a subject in the pre-clinical stage including mild cognitive impairment (MCI) or in a model animal. The model animal of cognitive impairment induced by amyloid β protein can be prepared using a known method. For example, a transgenic mouse which exhibits excessive expression of amyloid β protein or a mouse to which a solution of amyloid β protein in an artificial cerebrospinal fluid is administered can be used as such a model animal.

The "treatment" with the therapeutic agent or the therapeutic drug includes both therapeutic treatment and prophylactic treatment. The effect of the treatment includes prevention of occurrence or recurrence of the disease, amelioration of symptoms, suppression of progression of the disease, amelioration or reduction of symptoms, and recovery. The extent of the effect is not limited, and can be evaluated by known methods related to cognitive impairment induced by amyloid β protein or to Alzheimer's disease.

The method of administration of the therapeutic agent or the therapeutic drug according to the present invention is not limited as long as a desired effect can be obtained. Usually, as an in vivo method, an administration method which enables delivery of a predetermined peptide as an effective component to the cerebral ventricle, where amyloid β protein accumulates, is used. As an in vitro method, an addition method in which a predetermined peptide is added to a cell culture liquid to bring the peptide into contact with cultured nerve cells or the like is used.

Another possible therapeutic method is use of a virus vector for expressing p3-Alcβ37 or a part of its peptide sequence in cerebral nerve cells. As such a virus vector, for example, recombinant adeno-associated virus serotype 9 (AAV9), which can pass through the blood-brain barrier, may be used. Expression of a gene in central nerves and the glial cell system using AAV9 vector administered into blood is known. In cases where nerve cell-specific expression of p3-Alcβ37 is necessary, for example, the virus vector AAV9 in which the promoter region of the synapsin I gene is incorporated may be used. In order to allow expression of p3-Alcβ37 in cells and its secretion from the cells, for example, a precursor peptide sequence which is prepared by cleaving Alcadein β at the ε cleavage site and linked to a signal peptide sequence of 19 amino acids for Alcadein β is expressed. After the expression in the cells, the signal sequence is removed from the precursor peptide by cleavage by signal peptidase, and cleavage by γ-secretase proceeds from the ε-site to the γ-site, resulting in secretion of p3-Alcβ37 composed of 37 amino acids (Piao et al., PLoS One 8, e62431, 2013). Of course, as a method for allowing the expression and the secretion of the peptide, a known method other than this method, for example, a method in which a gene encoding the 37 amino acids produced by the cleavage at the γ-site is used from the beginning, may be used. In consideration of the efficiency of the expression and the secretion, a method effective for the treatment may be selected. By using a method in which a virus vector is introduced into blood, p3-Alcβ37 can be noninvasively introduced into the central nerve system, and the therapeutic effect can be assayed by a known method.

The dose of the therapeutic drug, that is, the amount of the effective component per administration and the number (frequency) of doses, may be controlled within an appropriate range taking into account the object; the age and the body weight of the subject to which the therapeutic drug is administered; the severity of the disease; the administration route; the pharmacokinetics; and/or the like.

—Method for Pathological Analysis—

The predetermined peptides in the present invention, that is, the peptides used in the first to sixth embodiments described above, may also be used in methods for pathological analysis of cognitive impairment induced by amyloid β protein, or Alzheimer's disease. That is, the method for pathological analysis of cognitive impairment induced by amyloid β protein according to the present invention comprises a step of administration of the predetermined peptide used in the present invention to a mammal (human, or a mammal other than human) which developed cognitive impairment induced by amyloid β protein or to a model animal (a mammal other than human) thereof, or a step of adding the peptide to a cultured nerve cell(s) as a model cell(s) thereof or to a biomolecule(s) expressed in a nerve cell(s). The method for pathological analysis of Alzheimer's disease according to the present invention comprises a step of administration of the predetermined peptide used in the present invention to a mammal (human, or a mammal other than human) which developed Alzheimer's disease or to a model animal (a mammal other than human) thereof, or a step of adding the peptide to a cultured nerve cell(s) as a model cell(s) thereof or to a biomolecule(s) expressed in a nerve cell(s).

Examples of the biomolecules expressed in nerve cells include proteins such as receptors expressed on the cell surface, and proteins associated with signal transduction expressed in the cytoplasm.

The model cells are cells which reproduce the disease state of, for example, degeneration of nerve cells (e.g., neurons) or the like caused by cognitive impairment induced by amyloid β protein or Alzheimer's disease. The model cells can be prepared from cultured nerve cells derived from human or a mammal other than human using a known method.

In such methods for pathological analysis, by observing and evaluating the reaction caused by administering or adding the predetermined peptide used in the present invention, the action mechanism of the therapeutic agent or the therapeutic drug using the peptide can be studied in detail. This enables development of means for enhancing the effects of therapeutic methods using them, and development of novel therapeutic agents and therapeutic drugs.

EXAMPLES

Methods

Preparation of a mouse model of memory disorder by administration of the amyloid β protein oligomer, and evaluation of the ability of memory acquisition by a novel object recognition test were carried out according to an earlier paper (Balducci et al., Proc Natl Acad Sci USA 107, 2295-2300, 2010).

ICR mice (6 to 7 weeks old) were anesthetized with ketamine (100 mg/kg) and xylazine (40 mg/kg), and each mouse was fixed on a brain stereotaxic apparatus. After removal of the scalp, small holes were made on the skull on the lateral ventricles, and guide cannulae (23 gage) were bilaterally embedded at the positions of ±1.0 mm lateral and 0.65 mm posterior to the bregma. The guide cannulae were fixed with a dental resin. After a period of four to five days for recovery from the surgery, each mouse was allowed to move freely for 10 minutes in order to allow acclimatization to the environment in a test cage (39 cm×22 cm) (habituation). This was continued for 3 days. On the next day, an artificial cerebrospinal fluid (control), artificial cerebrospinal fluid in Which 1 μM amyloid β protein oligomer is dissolved, or artificial cerebrospinal fluid in which 1 μM amyloid β protein oligomer and 10 μM p3-Alcβ37 peptide or a partial peptide thereof are dissolved, was bilaterally administered (3.5 μl/side) to the lateral ventricles through the guide cannulae embedded in the head, using an injection cannulae (30 gage, 1.7 mm from the brain surface).

Two hours after the administration, two identical objects (glass vials each having a plastic cap [objects A]: 3-cm diameter×6.5-cm height) were placed in the test cage for which the habituation had been carried out, such that the objects were positioned about 20 cm distant from each other. In the test cage, each mouse was allowed to move freely for 10 minutes to allow learning of the object A (training session). On the next day, 24 hours after the learning, a test was carried out to investigate if the mouse remembered the object A, which was presented on the previous day (test session). More specifically, in the same test cage, the object A presented on the previous day (that is, a familiar object) and a novel object (a metal cube [object B]: 4 cm×4 cm×4 cm) were placed at the same positions as those used on the previous day, and the mouse was allowed to move freely for 10 minutes in the test cage. In normal mice, since they naturally show interest in novel objects, the time for exploring the novel object (object B) is longer than the time for exploring the familiar object (object A). In contrast, mice whose ability to remember is impaired show almost the same length of exploration time for the object A and the object B in the test session, since the mice do not remember the object presented on the previous day (object A). The exploratory behavior for each object was recorded using a video camera, and the total exploration time for each object was calculated. The time spent for contacting or approach of the head to the object (including sniffing), and contacting of a forelimb or hindlimb with the object was included in the exploration time. The ability of memory acquisition of the mice in each group was represented using the discrimination index. The discrimination index was defined as follows: ([exploration time for novel object]−[exploration time for familiar object ])/([exploration time for novel object]+[exploration time for familiar object]). In cases where discrimination between the novel object and the familiar object is impossible, the discrimination index is 0, while in cases where the exploration time for the novel object is longer than the exploration time for the familiar object, the discrimination index is positive. When a novel object is presented to a mouse, the mouse becomes less interested in the object (shows less exploratory behavior for the novel object) as time passes. Therefore, the calculation of the exploration time and the discrimination index was carried out based on the behavior observed during the first 5 minutes after the placement of the mouse in the test cage.

Also for a mouse model of memory disorder prepared by administration of an NMDA receptor inhibitor MK-801, evaluation Of the ability of memory acquisition was carried out by a novel object recognition test. The experiment was carried out by same method as described above except for the following two conditions: (1) an artificial cerebrospinal fluid (control), or an artificial cerebrospinal fluid in which 10 μM p3-Alcβ37 peptide is dissolved, was administered to the cerebral ventricle; and (2) one and a half hours after the administration to the cerebral ventricle (that 30 minutes before placing the mouse into the test cage), (+)-MK-801 maleate (2 mg/kg) was intraperitoneally administered to induce NMDA receptor-dependent memory disorder.

In terms of the reagents used, the composition of the artificial cerebrospinal fluid was as follows: 137 mM NaCl, 3 mM KCl, 1 mM $MgCl_2$, 1.2 mM $CaCl_2$, 2.5 mM glucose, and 2 mM sodium phosphate buffer (pH 7.4). The amyloid β protein oligomer was prepared according to an earlier literature (Balducci et al., Proc Natl Acad Sci USA 107, 2295-2300, 2010). A stock solution of amyloid β protein (300 μM) was prepared as an aqueous solution in 0.02% trifluoroacetic acid, and stored at −25° C. The stock solution was used within one month after the preparation. The preparation of the amyloid β protein oligomer was carried out at the time of use as follows. After melting the amyloid β protein stock solution, the solution was alkalized with a solution of $NaOH:NH_3$=1:3 (pH>10.5), and the amyloid β protein was diluted with 50 mM phosphate-buffered saline (pH 7.4) to 100 μM. The resulting dilution was incubated at 22° C. for 18 hours. The solution was then diluted with the artificial cerebrospinal fluid to 1 μM, and administered to the cerebral ventricle as an amyloid β protein oligomer. The mixture of the oligomer and the p3-Alcβ37 peptide or the partial peptide thereof was prepared in the same manner as the procedure described above except that the p3-Alcβ37 peptide or the partial peptide thereof was also added to a final concentration of 10 μM when the incubated 100 μM amyloid β protein oligomer was diluted to 1 μM.

The sequences of the peptides used were as follows.

```
                                        (SEQ ID NO: 6)
amyloid-β42:
DAEFRHDSGYEVHHQKLVFFAEDVGSNKGAIIGLMVGGVVIA (SEQ ID NO: 1)
p3-Alcβ37:
VLSSQQFLHRGHQPPPEMAGHSLASSHRNSMIPSAAT (SEQ ID NO: 4)
p3-Alcβ[1-19]
VLSSQQFLHRGHOPPPEMA (SEQ ID NO: 5)
p3-Alcβ[20-37]:
GHSLASSHRNSMIPSAAT (SEQ ID NO: 3)
p3-Alcβ[1-11]:
VLSSQQFLHRG (SEQ ID NO: 2)
p3-Alcβ[9-19]:
HRGHQPPPEMA
```

The peptides used were obtained from the following: amyloid-β42 (Keck Biotechnology Resource Laboratory, Yale University), p3-AlcΘ37 (Keck Biotechnology Resource Laboratory, Yale University), p3-Alcβ[1-19] (Genemed Synthesis, and Peptide Institute), p3-Alcβ[20-37] (Genemed Synthesis, and Peptide Institute), p3-Alcβ[1-11] (Peptide Institute), and p3-Alcβ[9-19] (Peptide Institute).

Results

Figure 1:
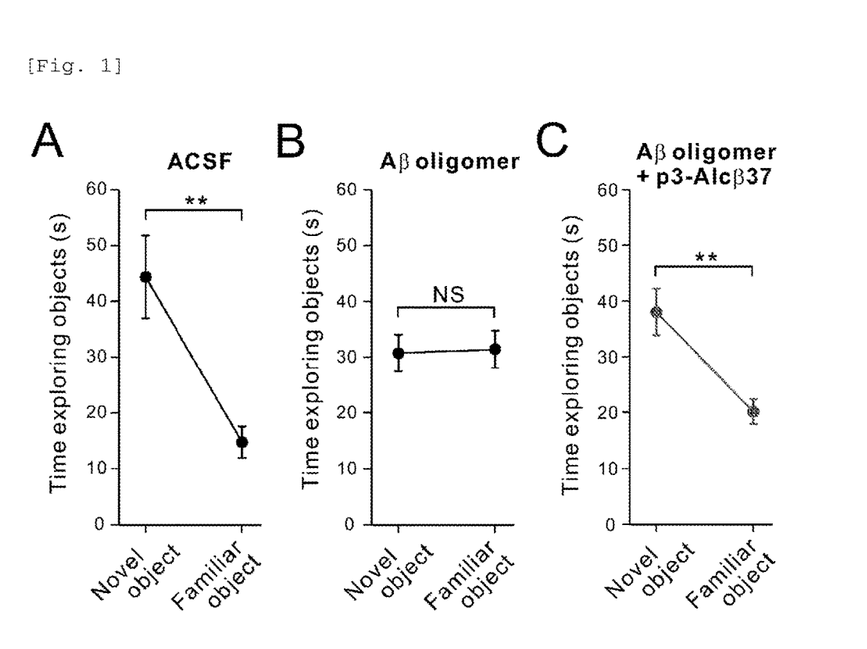
FIG. 1 shows the effect of the p3-Alcβ37 peptide on memory disorder induced by an amyloid β protein oligomer. Each graph shows the exploration times for a novel object and a familiar object measured in Examples. A (ACSF) : Artificial cerebrospinal fluid alone (control). B (Aβ oligomer): Artificial cerebrospinal fluid in which 1 μM amyloid β protein oligomer is dissolved. C (Aβ oligomer+p3-Alcβ37): Artificial cerebrospinal fluid in which 1 μM amyloid β protein oligomer and 10 μM p3-Alcβ37 peptide are dissolved. **: P<0.01.
Figure 2:
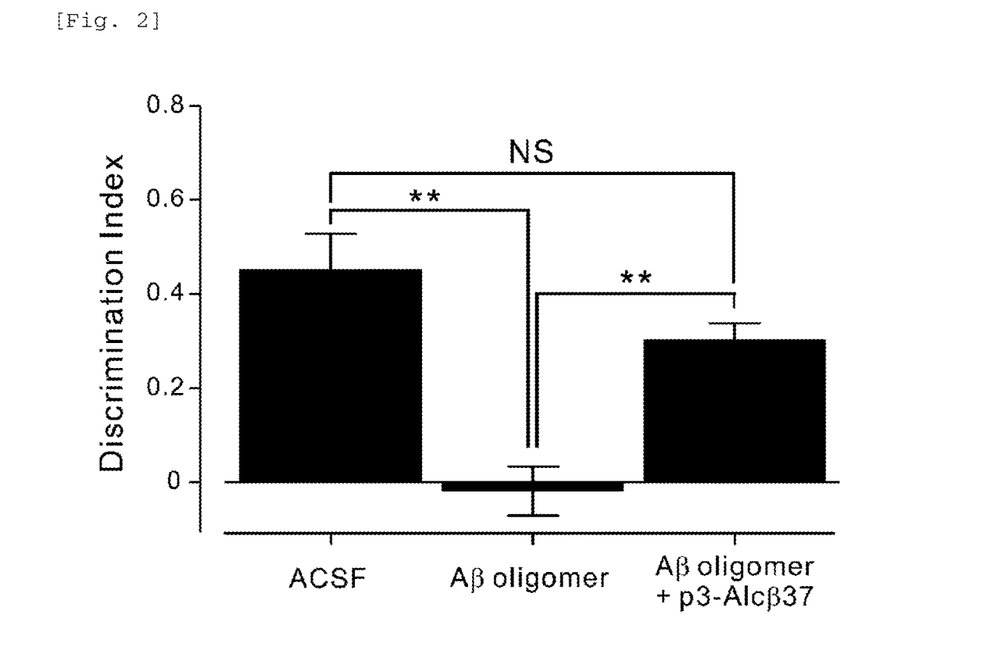
FIG. 2 shows the Change in the discrimination index due to administration of the p3-Alcβ37 peptide. The graph shows the discrimination index calculated from the results of Examples ( 1) according to the following equation.

In the mice to which the artificial cerebrospinal fluid was administered, the exploration time for the novel object B was significantly longer than the exploration time for the familiar object A (FIG. 1A; n=11 mice, P<0.01, paired t-test). That is, the memory was normally acquired. On the other hand, in the mice to which the amyloid β protein oligomer was administered, the exploration time was almost the same between the familiar object A and the novel object B (FIG. 1B; n=20 mice, P>0.05, paired t-test). That is, it was found that acquisition of the memory was completely impaired. The present inventors also found that the mice to which the mixture of the amyloid β protein oligomer and the p3-Alcβ37 peptide was administered showed remarkable recovery of the ability to remember (FIG. 1C; n=14 mice, P<0.01, paired t-test). In 2, the ability of memory acquisition in each group is represented using the discrimination index. Relative to the group in which the artificial cerebrospinal fluid was administered, the group in which the oligomer was administered showed a significant decrease in the discrimination index (FIG. 2; p<0.01, Tukey test). Relative to the group in which the oligomer was administered, the group in which the oligomer/p3-Alcβ37 mixture was administered showed a significant increase in the discrimination index ( 2; P<0.01, Tukey test). No significant difference in the discrimination index was found between the group in which the artificial cerebrospinal fluid was administered and the group in which the oligomer/p3-Alcβ37 mixture was administered (FIG. 2; P>0.05, Tukey test). These results indicate that the memory disorder induced by the amyloid β protein oligomer is drastically ameliorated by intracerebral administration of the p3-Alcβ37 peptide.

Figure 3:
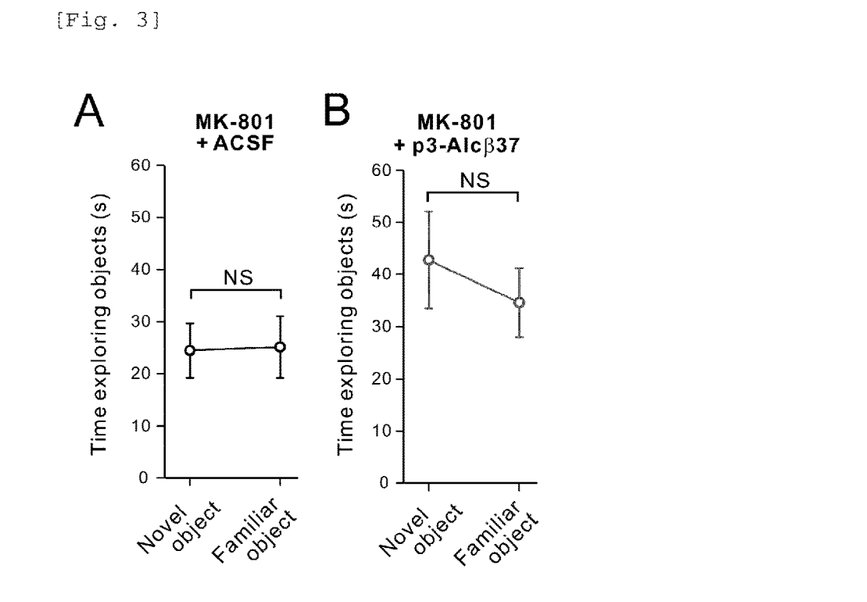
FIG. 3 shows the effect of the p3-Alcβ37 peptide on memory disorder induced by MK-801. Each graph shows the exploration times for a novel object and a familiar object measured in Examples. A (MK-801+ACSF): Administration of an artificial cerebrospinal fluid (control) to the cerebral ventricle, and intraperitoneal administration of MK-801. B (MK-801+p3-Alcβ37): Administration, to the cerebral ventricle, of an artificial cerebrospinal fluid in which 10 μM p3-Alcβ37 peptide is dissolved, and intraperitoneal administration of MK-801.

Subsequently, whether the action of p3-Alcβ37 to allow recovery from memory disorder is specific to the memory disorder caused by amyloid β protein, or the action also allows recovery from other memory disorders, was studied. It is well known that the NMDA receptor is indispensable for memory and learning. It is reported that gene knockout of the NMDA receptor (Rampon et al., Nat Neurosci 3, 238-244, 2000) or administration of an NMDA receptor inhibitor MK-801 (de Lima et al., Behav Brain Res 156, 139-143, 2005) causes impairment in novel object recognition tests. in view of this, also in the present study, MK-801 was intraperitoneally administered in the state where the artificial cerebrospinal fluid was administered to the cerebral ventricle. it was found, as a result, that the exploration time became almost the same between the familiar object A and the novel object B (FIG. 3A; n=8 mice, P>0.05, paired t-test). That is, acquisition of the memory was found to be impaired. Subsequently, MK-801 was intraperitoneally administered in the state where the p3-Alcβ37 peptide was administered to the cerebral ventricle. However, no remarkable difference in the exploration time was found between the familiar object A and the novel object B ( 3B; n=9 mice, P>0.05, paired t-test), so that the effect to ameliorate memory disorder was not found. Thus, it was shown that, although the p3-Alcβ37 peptide ameliorates memory disorder caused by amyloid β protein, the peptide is not capable of ameliorating memory disorder caused by inhibition of the NMDA receptor. This indicates that the p3-Alcβ37 peptide relatively selectively acts on amyloid β protein to ameliorate memory disorder.

Figure 4:
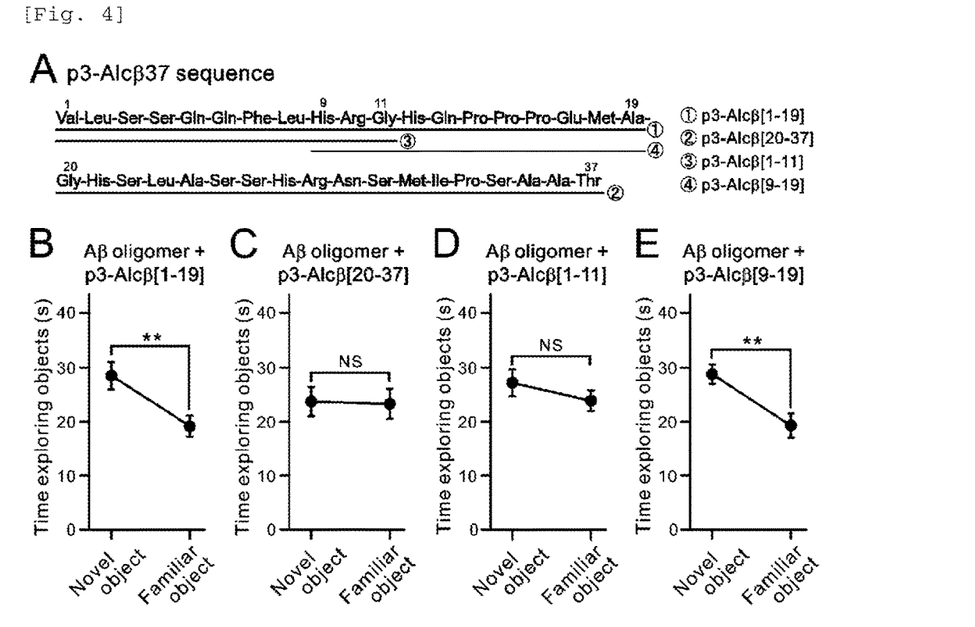

Finally, whether a partial peptide of p3-Alcβ37 is also capable of allowing recovery from memory disorder caused by the amyloid β protein oligomer was studied. In mice to which a mixture of the amyloid β protein oligomer and the partial peptide corresponding to positions 1 to 19 of p3-Alcβ37 (p3-Alcβ37 [1-19], FIG. 4A) was administered, remarkable recovery of the ability to remember was found (FIG. 4B; n=15 mice, P<0.01, paired t-test). In contrast, in mice to which a mixture of the oligomer and the partial peptide corresponding to positions 20 to 37 of p3-Alcβ37 (p3-Alcβ37 [20-37], FIG. 4A) was administered, no recovery of the ability to remember was found (FIG. 4C; n=16 mice, P>0.05, paired t-test). Subsequently, in view of this, the p3-Alcβ37 [1-19] peptide was further fragmented to prepare the partial peptide corresponding to positions 1 to 11 (p3-Alcβ37 [1-11], FIG. 4A) and the partial peptide corresponding to positions 9 to 19 (p3-Alcβ37 [9-19], 4A), and the prepared partial peptides were subjected to the study. As a result, while the ability to remember remained impaired in the case of the oligomer/p3-Alcβ37[1-11] (FIG. 4D; n=14 mice, P>0.05, paired t-test), the ability to remember showed remarkable recovery in the case of the oligomer/p3-Alcβ37 [9-19] (FIG. 4E; n=16 mice, P<0.01, paired t-test). These results indicate that p3-Alcβ37[9-19] (11 amino acids), which is a partial peptide of p3-Alcβ37, is also capable of ameliorating memory disorder caused by amyloid β protein.

SEQUENCE LISTING FREE TEXT

SEQ ID NO:1 p3-Alcβ37
SEQ ID NO:2 p3-Alcβ[9-19]/a part of p3-Alc beta 37 (positions 9-19)
SEQ ID NO:3 p3-Alcβ[1-11]/a part of p3-Alc beta 37 (positions 1-11)
SEQ ID NO:4 p3-Alcβ[1-19]/a part of p3-Alc beta 37 (positions 1-19)
SEQ ID NO:5 p3-Alcβ[20-37]/a part of p3-Alc beta 37 (positions 20-37)
SEQ ID NO:6 amyloid-β42

The invention claimed is:

1. A method for treatment of cognitive impairment induced by amyloid β protein or Alzheimer's disease, comprising:
   a step of administering an effective amount of a peptide selected from the group consisting of the following (I) to (VI) to a mammal which developed cognitive impairment induced by amyloid β protein or Alzheimer's disease, or to an animal model thereof:
   (I) a peptide consisting of the amino acid sequence of SEQ ID NO: 1: VLSSQQFLHRGHQPPPEMAGHSLASSHRNSMIPSAAT (SEQ ID NO: 1);
   (II) a peptide which is the amino acid sequence of SEQ ID NO: 1 except that one to three amino acids are altered by any one or more of deletion, addition, substitution, and side-chain modification;
   (III) a peptide which is a partial sequence of the amino acid sequence of SEQ ID NO: 1, comprising the amino acid sequence of SEQ ID NO: 2: HRGHQPPPEMA (SEQ ID NO: 2);
   (IV) a peptide which is a partial sequence of the amino acid sequence of SEQ ID NO: 1, comprising the amino acid sequence of SEQ ID NO: 2 except that one or two amino acids are altered by any one or more of deletion, addition, substitution, and side-chain modification;
   (V) a peptide which is the amino acid sequence of SEQ ID NO: 2 and a total of 1 to 50 amino acids added to the N-terminus and/or the C-terminus of the amino acid sequence of SEQ ID NO: 2 (excluding amino acid sequences which are identical to all or part of the amino acid sequence of SEQ ID NO: 1); and
   (VI) a peptide which is the amino acid sequence of SEQ ID NO: 2, except that one or two amino acids are altered by any one or more of deletion, addition (excluding addition to the N-terminus and/or the C-terminus), substitution, and side-chain modification and a total of 1 to 50 amino acids are added to the N-terminus and/or the C-terminus of said altered amino acid sequence.

* * * * *